United States Patent [19]

Kühle et al.

[11] 4,348,411
[45] Sep. 7, 1982

[54] COMBATING BACTERIA WITH HALOGENOMETHYLSULPHONYLPHENYL-PHTHALAMIC ACIDS

[75] Inventors: Engelbert Kühle, Bergisch-Gladbach; Peter Kraus, Cologne; Erich Klauke, Odenthal, all of Fed. Rep. of Germany

[73] Assignee: Bayer Aktiengesellschaft, Leverkusen, Fed. Rep. of Germany

[21] Appl. No.: 272,858

[22] Filed: Jun. 12, 1981

[30] Foreign Application Priority Data

Jul. 3, 1980 [DE] Fed. Rep. of Germany ....... 3025221

[51] Int. Cl.³ .................. C07C 147/13; A61K 31/195
[52] U.S. Cl. ..................................... 424/319; 562/430
[58] Field of Search ......................... 562/430; 424/319

[56] References Cited

U.S. PATENT DOCUMENTS 4,043,923  8/1977  Loudas et al. .................... 252/8.75

FOREIGN PATENT DOCUMENTS 1355849  6/1974  United Kingdom .

*Primary Examiner*—Robert Gerstl
*Attorney, Agent, or Firm*—Sprung, Horn, Kramer & Woods

[57] ABSTRACT

A halogenomethylsulphonylphenyl-phthalamic acid of the formula

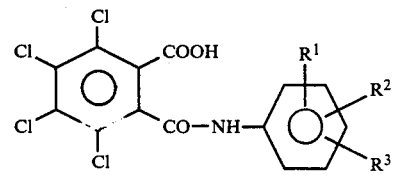

in which
$R^1$ represents a trihalogenomethylsulphonyl or dihalogenomethylsulphonyl group,
$R^2$ represents hydrogen, halogen or a lower alkyl or lower alkoxy group and
$R^3$ represents hydrogen, halogen or a lower alkyl, lower alkoxy, lower alkylmercapto or aroxy group, which group may be optionally substituted, or a salt thereof which possesses bactericidal, especially plant bactericidal, activity.

6 Claims, No Drawings

COMBATING BACTERIA WITH HALOGENOMETHYLSULPHONYLPHENYL-PHTHALAMIC ACIDS

The present invention relates to certain new halogenomethylsulphonylphenyl-phthalamic acids, to a process for their preparation and to their use as bactericides in plant protection.

It has already been disclosed that tetrachlorophthalamic acids have a cytobactericidal activity. Thus, N-(2,3-dichlorophenyl)-tetrachlorophthalamic acid has a bactericidal action against *Xanthomonas oryzae in the cultivation of rice* (see, for example, British Patent Specification No. 1,355,849). However, the activity is not always satisfactory when low concentrations are applied.

The present invention how provides, as new compounds, the halogenomethylsulphonylphenyl-phthalamic acids of the general formula

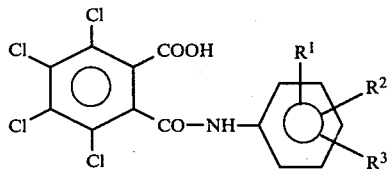

in which
  $R^1$ represents a trihalogenomethylsulphonyl or dihalogenomethylsulphonyl group,
  $R^2$ represents hydrogen, halogen or a lower alkyl or lower alkoxy group and
  $R^3$ represents hydrogen, halogen or a lower alkyl, lower alkoxy, lower alkylmercapto or aroxy group, which group may be optionally substituted.

Preferred "lower" groups are those with 1–4 carbon atoms.

The compounds of the formula (I) have powerful bactericidal actions. It is surprising that the compounds according to the invention have a better action against bacteria which are harmful to plants than the products which are known from the state of the art. The new compounds thus represent an enrichment of the art.

Preferred halogenomethylsulphonylphenyl-phthalamic acids of the formula (I) are those in which
  $R^1$ represents a trifluoromethylsulphonyl, difluorochloromethylsulphonyl or fluorodichloromethylsulphonyl group,
  $R^2$ represents hydrogen, chlorine, fluorine or a methyl or methoxy group and
  $R^3$ represents hydrogen, chlorine or a methyl, methoxy, methylmercapto or phenoxy group, which group may optionally be substituted by halogen and/or methyl and/or methoxy.

The invention also provides a process for the preparation of a halogenomethylsulphonylphenyl-phthalamic acid of the formula (I), in which tetrachlorophthalic anhydride, of the formula

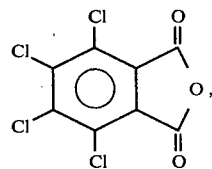

is reacted with an amine of the general formula

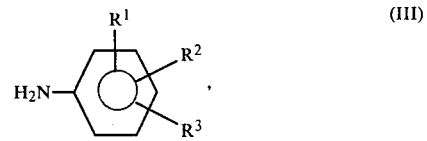

in which
  $R^1$, $R^2$ and $R^3$ have the abovementioned meanings, in the presence of a diluent.

If, for example, tetrachlorophthalic acid anhydride and 3-trifluoromethylsulphonylaniline are used for the preparation of the compounds according to the invention, the course of the reaction can be represented by the following equation:

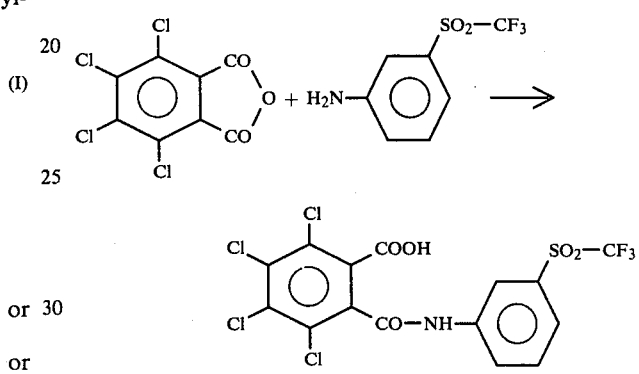

The formula (II) describes the generally known tetrachlorophthalic anhydride to be used as the starting substance.

The general formula (III) provides a definition of the amines also to be used as starting substances. In this formula, $R^1$, $R^2$ and $R^3$ preferably have the meanings given above as preferred for the general formula (I).

Amines of the formula (III) and their preparation are known and they can be prepared by processes which are known from the literature (in this context, see DE-OS (German Published Specification) 2,845,996). They are obtained, for example, when the corresponding nitro compounds are hydrogenated in a pressure vessel in a known manner at 50° C. under a pressure of 50 bars in the presence of a nickel catalyst; methanol is a suitable solvent.

The corresponding nitro compounds are obtained from fluoromethylmercapto-nitrobenzenes, which, as is known, can be oxidized to the fluoromethylsulphonyl-nitrobenzenes, for example in acetic acid solution; chromium trioxide can be used as the oxidizing agent and the oxidation proceeds at from about 80° to 90° C.

The following amines may be mentioned as examples of compounds of the formula (III): 2-, 3- or 4-trifluoromethylsulphonylaniline, 3-chloro-4-trifluoromethylsulphonyl-aniline, 2-, 3- or 4-difluorochloromethylsulphonyl-aniline, 4-fluorodichloromethylsulphonyl-aniline, 3-fluorodichloromethylsulphonyl-aniline and 3-chloro-4-difluoromethylsulphonyl-aniline.

Possible diluents in the process of this invention are any of the inert solvents. These include ethers, such as tetrahydrofuran and dioxane; hydrocarbons, such as toluene; chlorinated hydrocarbons, such as chloroform; ketones, such as acetone; or dimethylsulphoxide or sulpholane.

The reaction temperatures can be varied within a substantial range; the reaction is in general carried out at between 50° and 250° C., preferably at from 100° to 220° C.

Equimolar amounts are generally used for carrying out the process, but an excess of amine up to about 10% is not detrimental.

Working up is effected in the customary manner. The reaction products are crystalline compounds which can be isolated by filtration.

Instead of the free acid with the general formula (I), it is, of course, also possible to use salts thereof, for example the alkali metal salts and the ammonium salts.

The salts can easily be prepared from the acids (I) by adding the corresponding bases.

The active compounds according to the invention exhibit a powerful microbicidal action and can be employed in practice for combating undesired microorganisms. The active compounds are suitable for use as plant protection agents.

The compounds according to the invention are particularly active against bactericidal plant diseases.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

The compounds according to the invention are particularly effective against bacteria of the genus Xanthomonas, for example against *Xanthomonas oryzae* in rice. In combating bacterial diseases, it is advantageous that the compounds according to the invention exhibit systemic properties.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated alkphatic hydrocarbons, such as aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The present invention also provides a bactericidal composition containing as active ingredient a compound of the present invention in admixture with a solid or liquefied gaseous diluent or carrier or in admixture with a liquid diluent or carrier containing a surface-active agent.

The present invention also provides a method of combating bacteria which comprises applying to the bacteria, or to a habitat thereof, a compound of the present invention alone or in the form of a composition containing as active ingredient a compound of the present invention in admixture with a diluent or carrier.

The present invention further provides crops protected from damage by bacteria by being grown in areas in which immediately prior to and/or during the time of the growing a compound of the present invention was applied alone or in admixture with a diluent or carrier.

It will be seen from the usual methods of providing a harvested crop may be improved by the present invention.

PREPARATIVE EXAMPLES

EXAMPLE 1

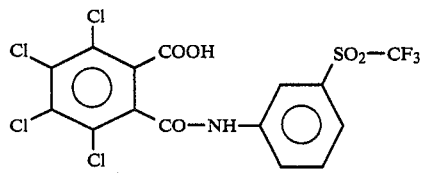
(1)

12.7 g (0.44 mol) of tetrachlorophthalic anhydride of melting point 255°–257° C. were dissolved in 100 ml of dioxane at 80°–257° C. were dissolved in 100 ml of dioxane at 80° C., and a solution of 10 g (0.45 mol) of 3-trifluoromethylsulphonyl-aniline in 50 ml of dioxan was added at this temperature. The reaction mixture was heated to the boiling point, and was kept at the boiling point for one hour. It was then allowed to cool and the reaction product was precipitated by adding ice-water. The product was filtered off, rinsed with methanol and dried. N-(3-Trifluoromethylsulphonyl-phenyl)-tetrachlorophthalamic acid had a melting point of 245°–246° C. The yield was 20.4 g, that is to say 92% of theory.

EXAMPLE 2

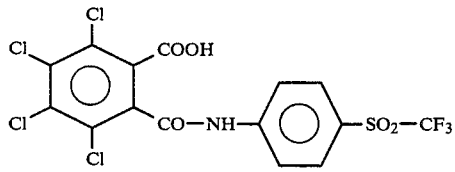
(2)

14 g (0.05 mol) of tetrachlorophthalic anhydride and 11 g (0.05 mol) of 4-trifluoromethylsulphonylaniline were heated to 200° C. and the mixture was kept at this temperature for 2 hours. It was then cooled and the reaction product was precipitated by adding ice-water. The product was then filtered off, washed with 50 ml of methanol and then stirred with 10% strength sodium hydroxide solution until it had dissolved. The impurities were filtered off and aqueous dilute hydrochloric acid was added to the filtrate. The crystals thereby obtained were filtered off and dried at 50° C. 14 g (that is to say 56% of theory) of N-(4-trifluoromethylsulphonyl-phenyl)-tetrachlorophthalamic acid of melting point 92°–97° C. were obtained.

The bactericidal activity of the compounds of this invention is illustrated by the following example:

EXAMPLE 3

*Xanthomonas oryzae* test/bacteriosis/rice/systemic
Solvent: 125 parts by weight of acetone
Emulsifier: 3.75 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for systemic properties, standard soil in which young plants had been grown was watered with 100 ml of the preparation of active compound. 3 days after the treatment, the plants were inoculated with an aqueous suspension of *Xanthomonas oryzae by pricking. Thereafter, the plants remained in a greenhouse at* 24° to 26° C. and 70 to 80% relative atmospheric humidity for 14 days until they were evaluated.

In this test, a clearly superior activity compared with the prior art was shown, for example, by the compound of Example 1.

It will be understood that the specification and examples are illustrative but not limitative of the present invention and that other embodiments within the spirit and scope of the invention will suggest themselves to those skilled in the art.

We claim:

1. A halogenomethylsulphonylphenyl-phthalamic acid of the formula 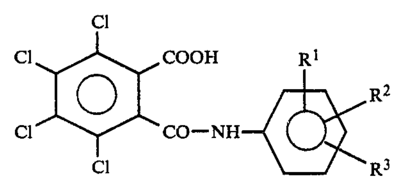 in which $R^1$ represents a trifluoromethylsulphonyl, difluorochloromethylsulphonyl or fluorodichloromethylsulphonyl group, $R^2$ represents hydrogen, chlorine, fluorine or a methyl or methoxy group and $R^3$ represents hydrogen, chlorine or a methyl, methoxy, methylmercapto or phenoxy group, which group may optionally be substituted by halogen and/or methyl and/or methoxy, or a salt thereof.

2. A compound according to claim 1, wherein such compound is N-(3-trifluoromethylsulphonylphenyl)-tetrachlorophthalamic acid of the formula 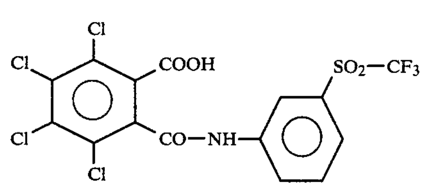 or a salt thereof.

3. A compound according to claim 1, wherein such compound is N-(4-trifluoromethylsulphonylphenyl)-tetrachlorophthalamic acid of the formula

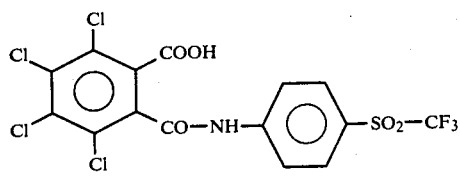

or a salt thereof.

4. A bactericidal composition comprising a bactericidally effective amount of a compound or salt according to claim 1 in admixture with a diluent.

5. A method of combating bacteria comprising applying to the bacteria, or to a habitat thereof, a bactericidally effective amount of a compound or salt according to claim 1.

6. The method according to claim 5, wherein such compound is
N-(3-trifluoromethylsulphonylphenyl)-tetrachlorophthalamic acid or
N-(4-trifluoromethylsulphonylphenyl)-tetrachlorophthalamic acid, or a salt thereof.

* * * * *

UNITED STATES PATENT AND TRADEMARK OFFICE
CERTIFICATE OF CORRECTION

PATENT NO. : 4,348,411
DATED : September 7, 1982
INVENTOR(S) : Englebert Kuhle et al It is certified that error appears in the above—identified patent and that said Letters Patent is hereby corrected as shown below:

| | |
|---|---|
| Col. 1, line 17 | Delete "how" insert --now-- |
| Col. 3, line 59 | Delete "alkphatic" and insert --aliphatic-- |
| Col. 3, line 60 | Before "aliphatic" insert omitted words --chlorobenzenes, chloroethylenes or methylene chloride-- |
| Col. 5, line 32 | After "80°" delete repeated words "-257° C. were dissolved in 100 ml of dioxane at 80°" |

Signed and Sealed this

Fourteenth Day of December 1982

[SEAL]

Attest:

GERALD J. MOSSINGHOFF

Attesting Officer    Commissioner of Patents and Trademarks